United States Patent
Harrison et al.

[11] Patent Number: 6,135,112
[45] Date of Patent: Oct. 24, 2000

[54] NON-SLIP CONDOM

[75] Inventors: Michael J. Harrison, Princeton; Frederick P. Sisbarro, Wayne; Steven R. Strauss, Hillsdale; Dennis R. Blum, Carteret; Jim D. Burns, Plainsboro, all of N.J.

[73] Assignee: Carter-Wallace, Inc., New York, N.Y.

[21] Appl. No.: 09/021,474

[22] Filed: Feb. 10, 1998

[51] Int. Cl.⁷ .................................................. A61F 6/04
[52] U.S. Cl. ............................................ 128/844; 128/918
[58] Field of Search .................................. 128/842, 844, 128/918; 604/347–353

[56] References Cited

U.S. PATENT DOCUMENTS

| | | | |
|---|---|---|---|
| D. 253,009 | 9/1979 | Okamoto | 128/844 |
| D. 254,808 | 4/1980 | Meldahl | 128/844 |
| 2,285,981 | 6/1942 | Johns | 2/21 |
| 3,130,721 | 4/1964 | Young | 128/844 |
| 3,809,090 | 5/1974 | Poviacs et al. | 128/349 |
| 4,576,156 | 3/1986 | Dyck et al. | 128/132 R |
| 4,798,600 | 1/1989 | Meadows | 128/844 |
| 5,036,863 | 8/1991 | Wheeler | 128/844 |
| 5,176,152 | 1/1993 | Wheeler | 128/844 |
| 5,361,779 | 11/1994 | Hess | 128/844 |
| 5,370,130 | 12/1994 | Hess | 128/844 |
| 5,398,699 | 3/1995 | Fergus | 128/844 |
| 5,425,379 | 6/1995 | Broad | 128/842 |
| 5,467,781 | 11/1995 | Kato | 128/844 |
| 5,490,519 | 2/1996 | Hessel | 128/844 |
| 5,579,784 | 12/1996 | Harari | 128/844 |

FOREIGN PATENT DOCUMENTS 1566365  4/1971  Germany.

*Primary Examiner*—Michael A. Brown
*Attorney, Agent, or Firm*—Kenneth Watov; Watov & Kipnes, P.C.

[57] ABSTRACT

A condom includes at least one ring above a ring at the opening of the condom, and at least one section of reduced inside diameter relative to other sections thereof between the open and a closed ends.

16 Claims, 2 Drawing Sheets

NON-SLIP CONDOM

RELATED APPLICATION

A related co-pending Application is Ser. No. 821,382, entitled "Multiple Ring Condom", that was filed on Mar. 20, 1997, the teachings of which are incorporated herein by reference to the extent they do not conflict herewith.

FIELD OF THE INVENTION

The present invention relates generally to condoms, and more particularly to condoms provided with non-slip features.

BACKGROUND OF THE INVENTION

Normally the condom is made of strong latex rubber, or some type of animal skin or a synthetic membrane such as polyurethane. Of necessity, in order to provide an acceptable level of tactile stimulation to the wearer, the condom must be quite thin. In general, it is elastically fitted to the male organ and during coitus remains stretched and taut. This stretched, taut condition of the condom can compromise the integrity of the condom insofar as leakage and slippage are concerned.

In accordance with the invention set forth in U.S. patent application Ser. No. 821,382 entitled "Multiple Ring Condom" that was filed on Mar. 20, 1997, is assigned to the same assignee herewith, and is incorporated herein by reference, methods were disclosed for improving the user protection and safety associated with condoms by adding one or more additional rings between the conventional or base ring at the opening of the condom and the closed end. Through use of this configuration, the incidence of slippage and leakage of the condom during use is substantially reduced, i.e., when following ejaculation the penis becomes flaccid, a possibility of leakage of seminal fluid and slippage of the condom occurs. It is believed that proper placement of the rings will provide clitoral stimulation. While the distance between rings on the condom is not critical, a distance of at least one-quarter inch between rings has been found to be suitable. It is believed but not yet proven that even a distance of four inches between rings may be suitable.

In general the rings formed on the condom will have approximately equal outside and inside diameters, but rings of different outside and inside diameters may be used, i.e., the additional rings above the base ring at the opening of the condom can have a smaller outside and inside diameter than that of the base ring to reduce slippage. There is a limit, however, to the degree to which the diameter of a ring can be reduced without being so tight on a penis as to be objectionable to the user.

SUMMARY OF THE INVENTION

In accordance with this invention, rings are added above the conventional ring at the opening of the condom to reduce slippage, and a further reduction in slippage of a condom during use is achieved by reducing the internal diameter of this condom for a portion of its length. Also, the thickness of the rings can be controlled to enhance the non-slippage property. In a preferred embodiment, this portion occurs at the open end and includes a ring, but in another embodiment it occurs intermediate the open and closed ends.

BRIEF DESCRIPTION OF THE DRAWINGS

Various embodiments of the present invention are described in detail below with reference to the accompanying drawings, in which like items are identified with the same reference designation, wherein.

DESCRIPTION OF THE INVENTION

In order to correlate the condoms of the drawings presented herein with the condoms described in the aforesaid Patent Application, corresponding rings are designated by the same numbers.

Figure 1:
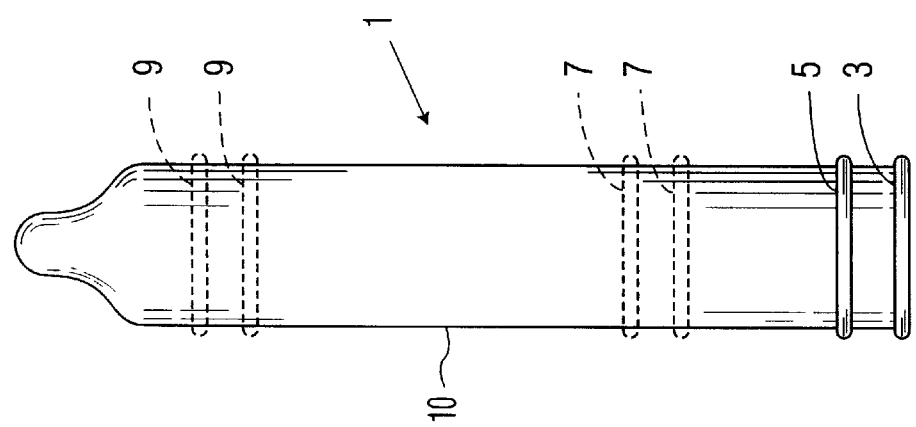
FIG. 1 shows a condom described and claimed in the aforesaid Patent Application.

In FIG. 1, a condom 1 includes a main body section 10, a ring 3 at its opening, a ring 5 above ring 3, and optionally a plurality of rings 7 and 9 above ring 5, as shown. The closed end 18 has a nipple-shape for providing a reservoir for semen, in this example, but can be otherwise shaped, such as not including a reservoir but having a blunt end. This design corresponds to that taught in the related Ser. No. 821,382 described above. However, in one embodiment of the present invention, the inventors recognized that by controlling the thickness of the rings non-slippage is enhanced, whereby a relatively thicker ring provides a tighter fit of the condom 1 on a penis.

Figure 2:
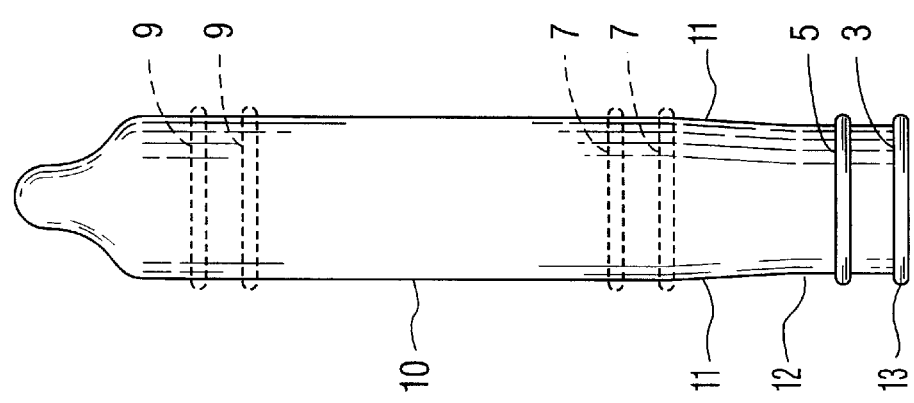
FIG. 2 illustrates a preferred embodiment of the invention wherein a section of a reduced diameter occurs at the open end of a condom.

Although not shown in FIG. 1, but as shown in FIG. 2, the outside and inside diameters of the ring 5 are typically less than the outside and inside diameters of the body 10, respectively, of the condom 1 so as to reduce slippage, but, as previously noted, there is a practical limit to the minimum inside diameter of ring 5. Also, there is a practical limit to the maximum thickness for a given ring 3, 5, 7, or 9. The thickness for a given ring is substantially equivalent to the difference between the outside and inside diameters of the ring.

In the preferred embodiment of the invention shown in FIG. 2, immediately below the closed end of the condom a main first section has a constant inside diameter, the inside diameter is reduced or tapered between points 11 and 12 of a second section to the inside diameter of the ring 5, and in a third section retains the diameter to the open end 13 where the ring 3 is located. This diameter reduction along the second section can be abrupt, but a smooth transition is preferred. The ring 5 is formed by rolling back material from the open end to a desired outside diameter. Ring 3 can be formed in the same manner as ring 5 as taught in the previously mentioned Ser. No. 821,382. Rings 7 and 9 are similarly formed. The friction of the section 12–13 of a reduced diameter adds to the friction provided by the ring 5, but because the condom is made of light material it does increase the sensation of tightness, but not in an objectional manner to a user.

Figure 3:
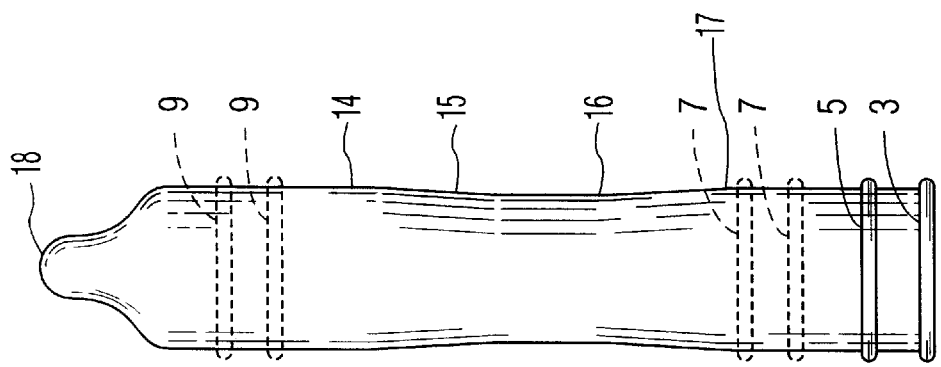
FIG. 3 illustrates another embodiment of the invention wherein a section of a reduced diameter occurs intermediate the closed and open ends of a condom.

FIG. 3 illustrates an embodiment of the invention wherein the condom has a first section 14 of constant diameter immediately below the closed end, and the diameter of the condom immediately below the first section is reduced or tapered between points 14 and 17 in a second section 15 to a smaller diameter which is retained in a third section 16, immediately below which the diameter gradually increases in a fourth section to the same diameter at the beginning of a fifth section 17 as the diameter of the first section 14. The fifth section 17 is of constant diameter proceeding down to the ring 3 at the open end, the inside diameter of ring 3 being the same as that of section 17. In one embodiment the diameter between points of sections 15 and 16 can be less than the inside diameter of the ring 5. In a condom made in accordance with FIG. 3, the outside diameter at the ring 9 was 36 mm for a glass mandrel (not shown) on which the condom of FIG. 3 was formed, for example. In a engineering prototype condom, the end of the first section 14 nearest one open end was at 67 mm from the nipple-shaped closed end 18, the tapered second section 15 had a length of 25 mm, the third section 16 had a length of 20 mm, the tapered fourth section had a length of 25 mm, and the length of the fifth section 17 was 43 mm, for example. The condom itself typically has a length of 180 mm±20 mm. This, of course, is an example of one condom design, but other condom designs may use different dimensions.

Figure 4:
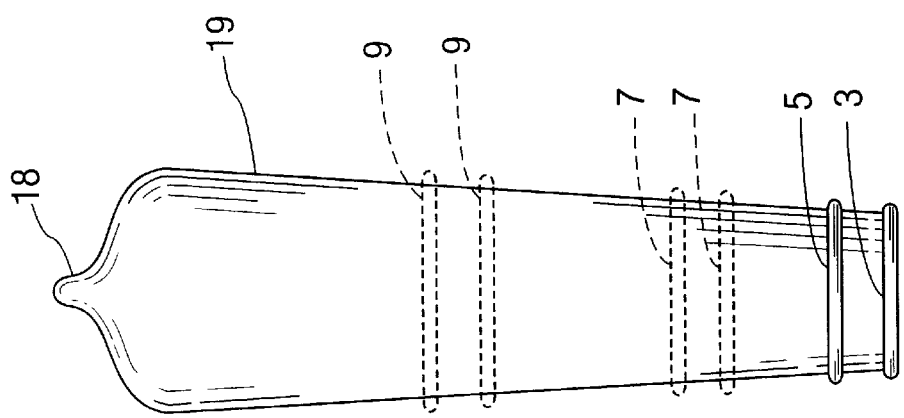
FIG. 4 illustrates a third embodiment of the invention for a condom having diverging side walls from its open to closed ends.

In FIG. 4, for a third embodiment of the invention, the condom has successively and linearly increasing diameter from its open end at ring 3 to its closed end 18, producing diverging sidewalls 19 from the open to closed ends. In addition to rings 3 and 5, different combinations of rings 7 and 9 may be added, depending upon the desired condom configuration.

Figure 5:
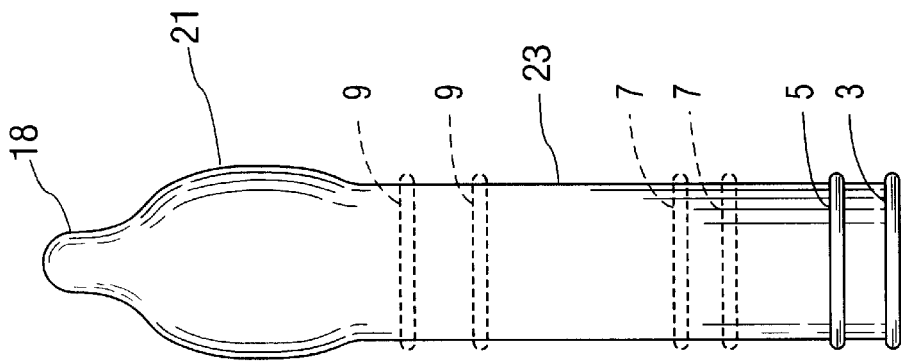
FIG. 5 shows a fourth embodiment of the invention for a condom having a bulbous body section near its closed end.

In FIG. 5, for a fourth embodiment of the invention, the condom has a bulbous body section proximate the closed end, followed by substantially parallel side wall sections 23 to the open end at ring 3. As in other embodiments, in addition to rings 3 and 5, different combinations of rings 7 and 9 may be added, dependent upon the desired condom product configuration.

Although, various embodiments of the invention have been shown and described herein, they are not meant to be limiting. Those of skill in the art may recognize certain modifications to these embodiments, which modifications are meant to be covered by the spirit and scope of the appended claims. For example, different combinations of specific features of the condom configurations of FIGS. 1 through 5 can be used to obtain other condom designs. One such other condom design is to include the bulbous body section 21 of the condom of FIG. 5, in combination with the narrowed body section 16 of the condom of FIG. 3. Also, the bodies of the condoms can be selectively textured as is known in the art, for each of the various embodiments of the invention.

What is claimed is:

1. A condom comprising:
a unitary substantially tubular body having opposing closed and open ends, including proceeding from said closed end to said open end, first, second, and third successive sections;
said first section having a constant first inside diameter;
said second section having a gradual linear reduction in inside diameter from said first diameter to a second inside diameter at an intersection with one end of said third section;
said third section having said second inside diameter constantly between said second section and said open end;
a first ring at said open end; and
a second ring adjacent said first ring having inside and outside diameters equal to, less than, or greater than those of said first ring, thereby controlling the relative thickness of the rings.

2. A condom as set forth in claim 1, wherein another end of said third section is adjacent said open end.

3. A condom as set forth in claim 1, further comprising:
said body further including a fourth section having one end integral with another end of said third section, said fourth section having a diameter that gradually linearly increases from said second diameter to said first diameter; and
said body further including a fifth section having one end integral with another end of said fourth section, said fifth section having said first diameter constantly between said fourth section and said open end.

4. A condom as set forth in claim 1, wherein said condom is made from material selected from the group consisting of latex rubber, animal skin, or a synthetic membrane.

5. A condom having a unitary tubular body comprising:
a closed end;
an open end;
a first section having a first end integral with said closed end, and a second end, said first section having a constant first inside diameter between its first and second ends;
a second section having a first end integral with said second end of said first section, said second section having an inside diameter that gradually linearly reduces to a second inside diameter at a second end thereof;
a third section having a first end integral with the second end of said second section, and a second end integral with said open end the diameter of said third section having a constant said second inside diameter between its first and second ends;
a first ring at said open end; and
a second ring in said third section.

6. A condom having a unitary tubular body comprising:
an open end and an opposite closed end;
continuous linearly diverging side walls from said open end to said closed end;
a first ring formed about said open end; and
at least a second ring formed between said open and closed ends.

7. The condom of claim 6, further including:
a plurality of other rings formed along said body and spaced apart from one another and from said first and second rings.

8. The condom of claim 6, wherein said condom is made from material selected form the group consisting of latex rubber, animal skin, and a synthetic membrane.

9. The condom of claim 6, further including a nipple-shaped reservoir for semen formed at the closed end.

10. A condom having a unitary tubular body comprising:
an open end and an opposite closed end;
a first ring formed about said open end;
parallel side walls continuously extending between said open and closed ends; and
at least a second ring formed between said open and closed ends, for enhancing non-slip properties of said condom, wherein the thickness of one of said first and second rings is made greater than the other for further enhancing the non-slip properties of said condom.

11. The condom of claim 10, further including a nipple-shaped reservoir for semen formed at the closed end.

12. The condom of claim 11, wherein said condom consists of material selected from the group consisting of latex rubber, animal skin, and a synthetic material.

13. A condom having a unitary tubular body comprising:

an open end and an opposite closed end;

a bulbous section having a first end integral with said closed end, and a second end;

a parallel walled section having a first end integral with said second end of said bulbous section, and a second end providing said open end;

a first ring formed about said open end; and at least a second ring formed on said parallel walled section, for enhancing non-slip properties of said condom.

14. The condom of claim 13, whereby the thickness of one of said first and second rings is made greater than the other, for further enhancing the non-slip properties of said condom.

15. The condom of claim 13, further including a nipple-shaped reservoir for semen formed at the closed end.

16. The condom of claim 13, wherein said condom is made from material selected from the group consisting of latex rubber, animal skin, or a synthetic membrane.

* * * * *